(12) United States Patent
Park et al.

(10) Patent No.: US 10,181,185 B2
(45) Date of Patent: Jan. 15, 2019

(54) IMAGE BASED SPECIMEN PROCESS CONTROL

(71) Applicant: KLA-Tencor Corporation, Milpitas, CA (US)

(72) Inventors: Allen Park, San Jose, CA (US); Lisheng Gao, Saratoga, CA (US); Ashok Kulkarni, San Jose, CA (US); Saibal Banerjee, Fremont, CA (US); Ping Gu, San Jose, CA (US); Songnian Rong, San Jose, CA (US); Kris Bhaskar, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 10 days.

(21) Appl. No.: 15/402,197

(22) Filed: Jan. 9, 2017

(65) Prior Publication Data
US 2017/0200264 A1 Jul. 13, 2017

Related U.S. Application Data

(60) Provisional application No. 62/277,457, filed on Jan. 11, 2016.

(51) Int. Cl.
*G06K 9/00* (2006.01)
*G06T 7/00* (2017.01)
*G01N 21/95* (2006.01)

(52) U.S. Cl.
CPC ....... *G06T 7/0004* (2013.01); *G01N 21/9501* (2013.01); *G06T 7/001* (2013.01); *G06T 2207/10056* (2013.01); *G06T 2207/10061* (2013.01); *G06T 2207/20081* (2013.01); *G06T 2207/20084* (2013.01); *G06T 2207/30148* (2013.01)

(58) Field of Classification Search
None
See application file for complete search history.

(56) References Cited

U.S. PATENT DOCUMENTS

| 6,891,627 B1 | 5/2005 | Levy et al. |
| 7,570,796 B2 | 8/2009 | Zafar et al. |
| 7,571,422 B2 | 8/2009 | Adel et al. |

(Continued)

FOREIGN PATENT DOCUMENTS

WO 2008-152020 12/2008

OTHER PUBLICATIONS

Hand et al., "Principles of Data Mining (Adaptive Computation and Machine Learning)," MIT Press, 2001, 578 pages.

(Continued)

*Primary Examiner* — Kevin Ky
(74) *Attorney, Agent, or Firm* — Ann Marie Mewherter

(57) ABSTRACT

Methods and systems for detecting anomalies in images of a specimen are provided. One system includes one or more computer subsystems configured for acquiring images generated of a specimen by an imaging subsystem. The computer subsystem(s) are also configured for determining one or more characteristics of the acquired images. In addition, the computer subsystem(s) are configured for identifying anomalies in the images based on the one or more determined characteristics without applying a defect detection algorithm to the images or the one or more characteristics of the images.

35 Claims, 4 Drawing Sheets

(56) References Cited

U.S. PATENT DOCUMENTS

| | | | |
|---|---|---|---|
| 7,676,077 B2 | 3/2010 | Kulkarni et al. | |
| 7,711,514 B2 | 5/2010 | Park et al. | |
| 7,904,845 B2 | 3/2011 | Fouquet et al. | |
| 8,126,255 B2 | 2/2012 | Bhaskar et al. | |
| 8,139,844 B2 | 3/2012 | Chen et al. | |
| 8,194,968 B2 | 6/2012 | Park et al. | |
| 8,559,001 B2 | 10/2013 | Chang et al. | |
| 8,594,823 B2 | 11/2013 | Park et al. | |
| 8,656,323 B2 | 2/2014 | Park et al. | |
| 8,664,594 B1 | 4/2014 | Jiang et al. | |
| 8,692,204 B2 | 4/2014 | Kojima et al. | |
| 8,698,093 B1 | 4/2014 | Gubbens et al. | |
| 8,716,662 B1 | 5/2014 | MacDonald et al. | |
| 8,826,200 B2 | 9/2014 | Park et al. | |
| 8,923,600 B2 | 12/2014 | Zafar et al. | |
| 8,948,495 B2 | 2/2015 | Marcuccilli et al. | |
| 9,002,497 B2 | 4/2015 | Volk et al. | |
| 9,087,367 B2 | 7/2015 | Chang et al. | |
| 9,151,712 B1 | 10/2015 | Adel et al. | |
| 9,170,209 B1 | 10/2015 | Chang et al. | |
| 9,222,895 B2 | 12/2015 | Duffy et al. | |
| 9,754,188 B2* | 9/2017 | Mei | G06F 17/30247 |
| 2003/0158679 A1* | 8/2003 | Fukushima | G06T 7/0004 |
| | | | 702/81 |
| 2004/0165761 A1* | 8/2004 | Hung | G03F 7/7065 |
| | | | 382/141 |
| 2005/0004774 A1 | 1/2005 | Volk et al. | |
| 2007/0288219 A1 | 12/2007 | Zafar et al. | |
| 2008/0077894 A1 | 3/2008 | Adel et al. | |
| 2008/0081385 A1 | 4/2008 | Marella et al. | |
| 2008/0163140 A1 | 7/2008 | Fouquet et al. | |
| 2009/0043527 A1 | 2/2009 | Park et al. | |
| 2009/0279772 A1 | 11/2009 | Sun et al. | |
| 2010/0266195 A1* | 10/2010 | Iwanaga | G06K 9/4652 |
| | | | 382/149 |
| 2010/0278440 A1* | 11/2010 | Dragovich | G01N 23/046 |
| | | | 382/218 |
| 2011/0187848 A1 | 8/2011 | Choi et al. | |
| 2012/0117010 A1* | 5/2012 | Ono | G06T 7/001 |
| | | | 706/20 |
| 2012/0216169 A1 | 8/2012 | Park et al. | |
| 2012/0316855 A1 | 12/2012 | Park et al. | |
| 2013/0035876 A1 | 2/2013 | Huang et al. | |
| 2013/0182100 A1 | 7/2013 | Aiko et al. | |
| 2013/0215258 A1* | 8/2013 | Gaglin | H04N 7/18 |
| | | | 348/87 |
| 2013/0318485 A1 | 11/2013 | Park et al. | |
| 2014/0193065 A1 | 7/2014 | Chu et al. | |
| 2014/0199791 A1 | 7/2014 | Park et al. | |
| 2014/0376801 A1* | 12/2014 | Karsenti | G06T 7/001 |
| | | | 382/145 |
| 2015/0064813 A1* | 3/2015 | Ayotte | H01L 22/12 |
| | | | 438/16 |
| 2015/0120220 A1 | 4/2015 | Wu et al. | |
| 2015/0124247 A1 | 5/2015 | Park et al. | |
| 2015/0154746 A1 | 6/2015 | Zafar et al. | |
| 2015/0178914 A1 | 6/2015 | Marella et al. | |
| 2015/0204798 A1* | 7/2015 | Nygaard | G01N 21/952 |
| | | | 356/237.2 |
| 2015/0332452 A1* | 11/2015 | Tsuchiya | G06T 7/0004 |
| | | | 382/147 |
| 2016/0314818 A1* | 10/2016 | Kirk | G11B 27/031 |
| 2017/0076451 A1* | 3/2017 | Pauly | G16H 50/20 |
| 2017/0323435 A1* | 11/2017 | Minekawa | G06T 7/001 |

OTHER PUBLICATIONS

International Search Report and Written Opinion for PCT/US2017/012890 dated Apr. 21, 2017.

Jebara, "Discriminative, Generative, and Imitative Learning," MIT Thesis, 2002, 212 pages.

Krizhevsky et al., "ImageNet Classification with Deep Convolutional Neural Networks," NIPS, 2012, 9 pages.

Sugiyama, "Introduction to Statistical Machine Learning," Morgan Kaufmann, 2016, 534 pages.

U.S. Appl. No. 15/176,139, filed Jun. 7, 2016 by Zhang et al. (submitted as U.S. Patent Application Publication No. 2017/0148226 published May 25, 2017 by Zhang et al.).

* cited by examiner

IMAGE BASED SPECIMEN PROCESS CONTROL

BACKGROUND OF THE INVENTION

1. Field of the Invention

The present invention generally relates to methods and systems for image based specimen process control.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on specimens to drive higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Defect review typically involves re-detecting defects detected as such by an inspection process and generating additional information about the defects at a higher resolution using either a high magnification optical system or a scanning electron microscope (SEM). Defect review is therefore performed at discrete locations on specimens where defects have been detected by inspection. The higher resolution data for the defects generated by defect review is more suitable for determining attributes of the defects such as profile, roughness, more accurate size information, etc.

Metrology processes are also used at various steps during a semiconductor manufacturing process to monitor and control the process. Metrology processes are different than inspection processes in that, unlike inspection processes in which defects are detected on specimens, metrology processes are used to measure one or more characteristics of the specimens that cannot be determined using currently used inspection tools. For example, metrology processes are used to measure one or more characteristics of specimens such as a dimension (e.g., line width, thickness, etc.) of features formed on the specimens during a process such that the performance of the process can be determined from the one or more characteristics. In addition, if the one or more characteristics of the specimens are unacceptable (e.g., out of a predetermined range for the characteristic(s)), the measurements of the one or more characteristics of the specimens may be used to alter one or more parameters of the process such that additional specimens manufactured by the process have acceptable characteristic(s).

Metrology processes are also different than defect review processes in that, unlike defect review processes in which defects that are detected by inspection are re-visited in defect review, metrology processes may be performed at locations at which no defect has been detected. In other words, unlike defect review, the locations at which a metrology process is performed on specimens may be independent of the results of an inspection process performed on the specimens. In particular, the locations at which a metrology process is performed may be selected independently of inspection results.

Currently, process control and yield analysis is performed using inline inspection and metrology such as that described above. Defects may be defined mainly by using one or more inspection parameters above a certain threshold. In other words, events from defect inspection must be above a certain threshold to be reported as defects. In most cases, these reported events are being used to identify locations on wafers as defective. For example, a gray level difference of 31 would be reported as a defect if the threshold for gray level difference is set to 30. These defects are then used to classify and identify potential mode failures in processes or tools. Defects can then be classified and used for isolating problems in semiconductor manufacturing. However, the definition of defect thresholds is limited to values set based on operating parameters within the inspection.

Due to the subtlety in manifestation of pattern deformation or random defects, some marginal events that are critical to device performance may be hidden in the data and never be detected as defects. Subtle defects or deformation in patterns may be binned as nuisance or non-critical defects. In addition, for advanced designs with tighter geometry and smaller process window, some critical defects can be undetected using traditional defect thresholds. Certain characteristics (which may be described as a combination of many optical attributes) in printed images may impact device performance but it is difficult to define a threshold to detect them as defects. Certain subtle failure modes can only be identified by extracting multiple attributes from inspection images (optical or SEM) and performing analysis such as data mining or advanced correlation techniques.

Such definitions of defects also depend upon the response variables (such as parametric test data or functional test) and at the time of defect reporting, it is not practical to use image characteristics as metrics to define defects. For example, critical defects may be defined by visual failure such as open, short, pattern deformation, size of defect etc. and correlation to electrical test such as parametric or functional tests or failure analysis. One of the key limitations in the currently used methods is that inspection data has to be binned (e.g., sizing) or classified (shapes, nuisance, real, etc.) before being used for device characterization and yield improvement work and therefore uses mostly supervised approaches. Inspection images (both optical and SEM images) contain a lot of information that is not being fully utilized for device characterization and yield learning.

Some currently available systems are configured to acquire images for post processing applications. For example, some currently used systems are configured for acquiring image patches associated with defects in wafer inspection lot results. The image acquisition only provides image patches of the locations in which one or more defects are detected. Such image acquisition also does not have the capability to acquire arbitrary images of interest that greatly limits the usefulness of the image post-processing applications. Some other currently used systems are configured for acquiring image patches from electron beam review results. Such image acquisition only provides limited data samples due to relatively low wafer coverage in electron beam review. Some image acquisition may be performed using entire swaths of image data stored in a storage medium.

Such image acquisition may capture whole swath images that provide the maximum information for the post processing applications. However, this method can only provide limited image data sets due to the extremely large data size (e.g., 40 TB of data per full wafer scan at nominal inspection pixel size on some currently used inspection tools). This practical constraint limits the usefulness of the post processing applications. In addition, there is no existing computing infrastructure to enable the image post processing applications using the above acquired images as well as associated data from multiple data sources at once.

Accordingly, it would be advantageous to develop systems and methods for detecting anomalies in images of a specimen that do not have one or more of the disadvantages described above.

SUMMARY OF THE INVENTION

The following description of various embodiments is not to be construed in any way as limiting the subject matter of the appended claims.

One embodiment relates to a system configured to detect anomalies in images of a specimen. The system includes an imaging subsystem configured for generating images of a specimen by directing energy to and detecting energy from the specimen. The imaging subsystem includes at least one energy source configured for generating the energy directed to the specimen and at least one detector configured for detecting the energy from the specimen. The system also includes one or more computer subsystems coupled to the imaging subsystem. The computer subsystems(s) are configured for acquiring the images generated of the specimen. The computer subsystem(s) are also configured for determining one or more characteristics of the acquired images. In addition, the computer subsystem(s) are configured for identifying anomalies in the images based on the one or more determined characteristics without applying a defect detection algorithm to the images or the one or more characteristics of the images. The system may be further configured as described herein.

Another embodiment relates to a computer-implemented method for detecting anomalies in images of a specimen. The method includes generating images of a specimen by directing energy to and detecting energy from the specimen with an imaging subsystem. The imaging subsystem includes at least one energy source configured for generating the energy directed to the specimen and at least one detector configured for detecting the energy from the specimen. The method also includes acquiring the images generated of the specimen. In addition, the method includes determining one or more characteristics of the acquired images. The method further includes identifying anomalies in the images based on the one or more determined characteristics without applying a defect detection algorithm to the images or the one or more characteristics of the images. The acquiring, determining, and identifying steps are performed by one or more computer subsystems coupled to the imaging subsystem.

Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on one or more computer systems for performing a computer-implemented method for detecting anomalies in images of a specimen. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
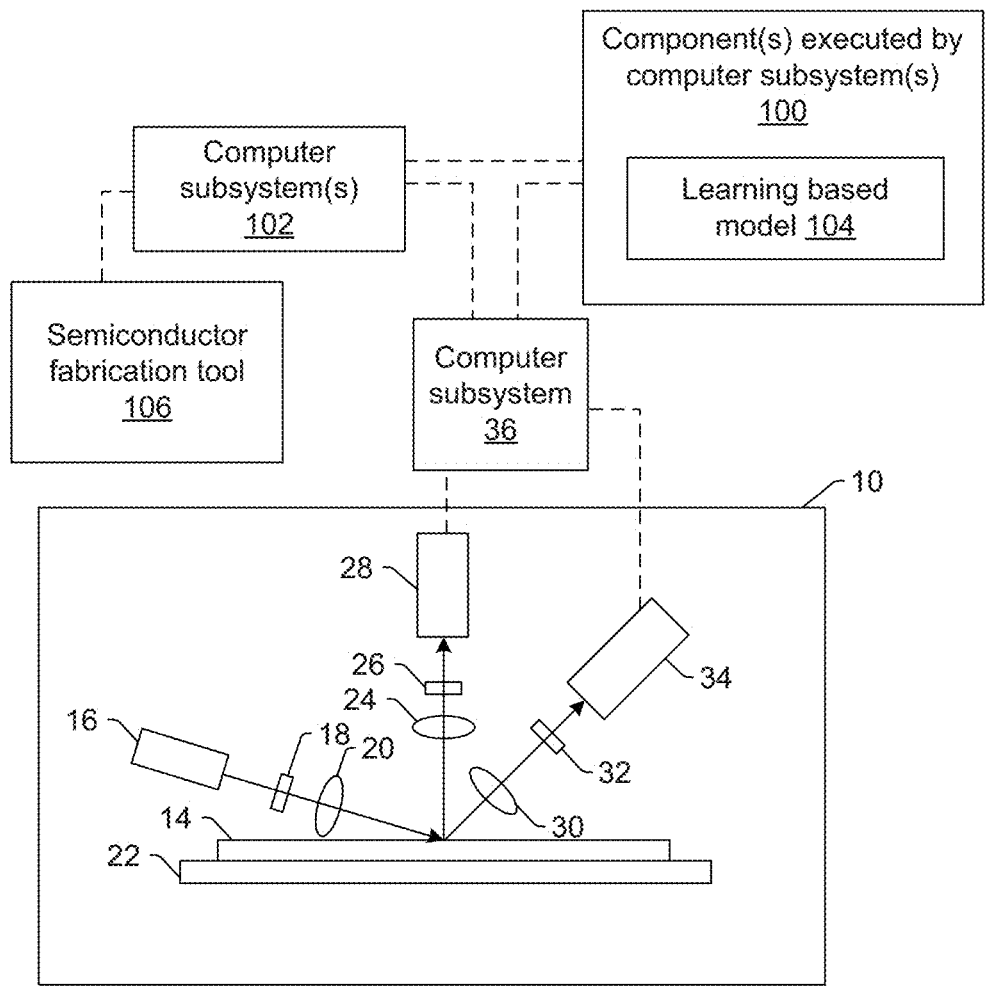
FIGS. 1 and 1a are schematic diagrams illustrating side views of embodiments of a system configured as described herein.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The tennis "design," "design data," and "design information" as used. interchangeably herein generally refer to the physical design (layout) of an IC and data derived from the physical design through complex simulation or simple geometric and Boolean operations. In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In addition, the "design," "design data," and "design information" described herein refers to information and data that is generated by semiconductor device designers in a design process and is therefore available for use in the embodiments described herein well in advance of printing of the design on any physical specimens such as reticles and wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

In general, the embodiments described herein are configured for image based specimen (e.g., wafer or reticle) process control. For example, one embodiment relates to a system configured to detect anomalies in images of a specimen.

As so-called "one-dimensional (1D) designs" are becoming more prevalent in semiconductor device designs, traditional approaches for identifying systematic and random defects may not provide enough sensitivity to process variation and impact to device performance. For example, in 1D, the definition of hot spots is somewhat different than previously used hot spots because all patterns are fairly uniform. In contrast, in two-dimensional (2D) designs, often times, there are substantially unique structures that tend to fail. Failures in 1D may not be readily described by simple characteristics. As such, the embodiments described herein may use the machine learning techniques described herein to find What is unique about certain locations in the design. However, use of the embodiments described herein is not limited to 1D designs.

For random defects, minimum defect size required to be captured is getting smaller. For systematic defects, millions and billions of identical or similar patterns are being printed on specimens making it difficult to identify unique pattern types that are considered to be hot spots. It is also difficult to define what level of deformation impacts device performance. Any excursion or anomalies (relatively small variation from typical values) must be identified from a relatively high volume of inspection data and analyzed appropriately to monitor the health of a process and process tool(s). As such, inspection signal (not just defect) will become an integral part of fab monitoring.

Hence, the embodiments described herein are configured to use inspection data such as optical inspection data and characteristics as part of overall fab data analysis to identify issues in semiconductor devices early to deter yield loss. Inspection tools such as those commercially available from KLA-Tencor, Milpitas, Calif. generate a lot of data in addition to reporting defects, and inspection parameters and images are unique and proprietary in solving difficult yield improvement and device characterization.

One embodiment of a system is shown in FIG. 1. The system includes an imaging subsystem configured for generating images of a specimen by directing energy to and detecting energy from the specimen. The imaging subsystem includes at least one energy source configured tor generating the energy directed to the specimen and at least one detector configured for detecting the energy from the specimen.

In some embodiments, the imaging subsystem is configured as an optical based imaging subsystem. For example, the system may include optical based imaging subsystem 10. In this manner, the at least one energy source may include at least one light source, and the at least one detector may include at least one light based detector. In addition, the energy directed to and detected from the specimen may include light. In the embodiment of FIG. 1, the optical based imaging subsystem is configured for scanning light over or directing light to a physical version of the specimen while detecting light from the specimen to thereby generate the images for the specimen. The optical based imaging subsystem may also be configured to perform the scanning (or directing) and the detecting with multiple modes as described further herein.

In one embodiment, the specimen is a wafer. The wafer may include any wafer known in the art, In another embodiment, the specimen is a reticle. The reticle may include any reticle known in the art.

In the embodiment of the system shown in FIG. 1, optical based imaging subsystem 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to specimen 14 at an oblique angle of incidence. The oblique angle of incidence may include any suitable oblique angle of incidence, which may vary depending on, for instance, characteristics of the specimen.

The optical based imaging subsystem may be configured to direct the light to the specimen at different angles of incidence at different times. For example, the optical based imaging subsystem may be configured to alter one or more characteristics of one or more elements of the illumination subsystem such that the light can be directed to the specimen at an angle of incidence that is different than that shown in FIG. 1. In one such example, the optical based imaging subsystem may be configured to move light source 16, optical element 18, and lens 20 such that the light is directed to the specimen at a different oblique angle of incidence or a normal (or near normal) angle of incidence.

In some instances, the optical based imaging subsystem may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused onto specimen 14 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the optical based imaging subsystem may be configured to alter one or more of the elements of the illumination subsystem based on the type of illumination to be used for imaging.

The optical based imaging subsystem may also include a scanning subsystem configured to cause the light to be scanned over the specimen. For example, the optical based imaging subsystem may include stage 22 on which specimen 14 is disposed during imaging. The scanning subsystem may include any suitable mechanical and/or robotic assembly (that includes stage 22) that can be configured to move the specimen such that the light can be scanned over the specimen. In addition, or alternatively, the optical based imaging subsystem may be configured such that one or more optical elements of the optical based imaging subsystem perform some scanning of the light over the specimen. The light may be scanned over the specimen in any suitable fashion such as in a serpentine-like path or in a spiral path.

The optical based imaging subsystem further includes one or more detection channels. At least one of the one or more detection channels includes a detector configured to detect light from the specimen due to illumination of the specimen by the optical based imaging subsystem and to generate output responsive to the detected light. For example, the optical based imaging subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, both detection channels are configured to detect scattered light, and the detection channels are configured to detect light that is scattered at different angles from the specimen. However, one or more of the detection channels may be configured to detect another type of light from the specimen (e.g., reflected light).

As further shown in FIG. 1, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 30, element 32, and detector 34 may be configured to collect and detect light that is scattered out of the plane of incidence. Therefore, such a detection channel may be commonly referred to as a "side" channel, and such a side channel may be centered in a plane that is substantially perpendicular to the plane of incidence.

Although FIG. 1 shows an embodiment of the optical based imaging subsystem that includes two detection channels, the optical based imaging subsystem may include a different number of detection channels (e.g., only one detection channel or two or more detection channels). In one such instance, the detection channel formed by collector 30, element 32, and detector 34 may form one side channel as described above, and the optical based imaging subsystem may include an additional detection channel (not shown) formed as another side channel that is positioned on the opposite side of the plane of incidence. Therefore, the optical based imaging subsystem may include the detection channel that includes collector 24, element 26, and detector 28 and that is centered in the plane of incidence and configured to collect and detect light at scattering angle(s) that are at or close to normal to the specimen surface. This detection channel may therefore be commonly referred to as a "top" channel, and the optical based imaging subsystem may also include two or more side channels configured as described above. As such, the optical based imaging subsystem may include at least three channels (i.e., one top channel and two side channels), and each of the at least three channels has its own collector, each of which is configured to collect light at different scattering angles than each of the other collectors.

As described further above, each of the detection channels included in the optical based imaging subsystem may be configured to detect scattered light. Therefore, the optical based imaging subsystem shown in FIG. 1 may be configured for dark field (DF) imaging of specimens. However, the optical based imaging subsystem may also or alternatively include detection channels) that are configured for bright field (BF) imaging of specimens. In other words, the optical based imaging subsystem may include at least one detection channel that is configured to detect light specularly reflected from the specimen. Therefore, the optical based imaging subsystems described herein may be configured for only DF, only BF, or both DF and BF imaging. Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art, For example, the detectors may include photo-multiplier tubes (PMTs), charge coupled devices (CCDs), time delay integration (TDI) cameras, and any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the optical based imaging subsystem may be signals or data, but not image signals or image data. In such instances, a computer subsystem such as computer subsystem 36 may be configured to generate images of the specimen from the non-imaging output of the detectors. However, in other instances, the detectors may be configured as imaging detectors that are configured to generate image signals or image data. Therefore, the optical based imaging subsystem may be configured to generate the images described herein in a number of ways.

It is noted that FIG. 1 is provided herein to generally illustrate a configuration of an optical based imaging subsystem that may be included in the system embodiments described herein or that may generate images that are used by the system embodiments described herein. Obviously, the optical based imaging subsystem configuration described herein may be altered to optimize the performance of the optical based imaging subsystem as is normally performed when designing a commercial optical based system. In addition, the systems described herein may be implemented using an existing optical based system (e.g., by adding functionality described herein to an existing system) such as the 29xx/39xx and Puma 9xxx series of tools that are commercially available from KLA-Tencor, Milpitas, Calif. For some such systems, the embodiments described herein may be provided as optional functionality of the system (e.g., in addition to other functionality of the system). Alternatively, the optical based imaging subsystem described herein may be designed "from scratch" to provide a completely new optical based system.

The system also includes one or more computer subsystems computer subsystem 36 and/or computer subsystem(s) 102) coupled to the imaging subsystem. For example, computer subsystem 36 may be coupled to the detectors of the optical based imaging subsystem in any suitable manner (e.g., via one or more transmission media, which may include "wired" and/or "wireless" transmission media) such that the computer subsystem can receive the output generated by the detectors during scanning of the specimen. Computer subsystem 36 and/or computer subsystem(s) 102 may be configured to perform a number of functions described further herein using the output of the detectors.

The computer subsystems shown in FIG. 1 (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 as shown by the dashed line in FIG. 1 by any suitable transmission media, which may include any suitable wired and/or wireless transmission media known in the art. Two or more of such computer subsystems may also be effectively coupled by a shared computer-readable storage medium (not shown).

Figure 1A:
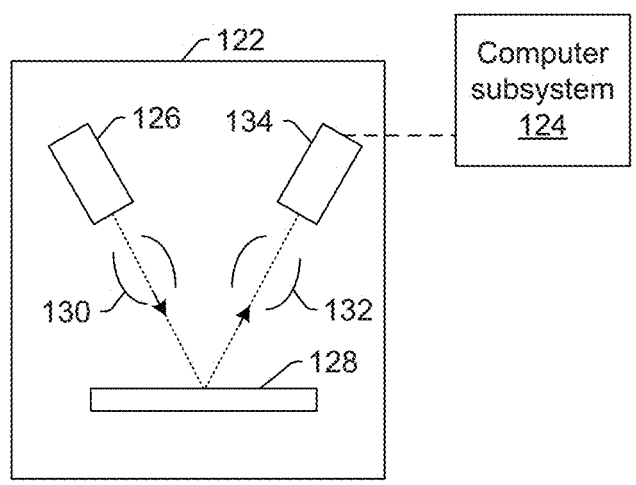

Although the imaging subsystem is described above as being an optical or light-based imaging subsystem, the imaging subsystem may be configured as an electron beam based imaging subsystem. For example, in one embodiment, the images generated for the specimen includes electron beam based images. In addition, the at least one energy source may include at least one electron beam source, and the at least one detector may include at least one electron beam based detector. In this manner, the energy directed to the specimen may include electrons, and the energy detected from the specimen may include electrons. In one such embodiment shown in FIG. 1*a*, the electron beam based imaging subsystem includes electron column 122 coupled to computer subsystem 124. As also shown in FIG. 1*a*, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 1*a* as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam based imaging subsystem may be configured to use multiple modes to generate electron beam based images for the specimen as described further herein (e.g., with different illumination angles, collection angles, etc.). The multiple modes of the electron beam based imaging subsystem may be different in any imaging parameters of the imaging subsystem.

Computer subsystem 124 may be coupled to detector 134 as described above. The detector may detect electrons returned from the surface of the specimen thereby forming electron beam based images for the specimen. The electron beam based images may include any suitable electron beam based images. Computer subsystem 124 may be configured to perform one or more functions described further herein for the specimen using images generated by detector 134. Computer subsystem 124 may be configured to perform any additional step(s) described herein. A system that includes the electron beam based imaging subsystem shown in FIG. 1a may be further configured as described herein.

It is noted that FIG 1a is provided herein to generally illustrate a configuration of an electron beam based imaging subsystem that may be included in the embodiments described herein. As with the optical based imaging subsystem described above, the electron beam based imaging subsystem configuration described herein may be altered to optimize the performance of the electron beam based imaging subsystem as is normally performed when designing a commercial electron beam based system. In addition, the systems described herein may be implemented using an existing electron beam based imaging subsystem (e.g., by adding functionality described herein to an existing electron beam based system) such as the eSxxx and eDR-xxxx series of tools that are commercially available from KLA-Tencor. For some such systems, the embodiments described herein may be provided as optional functionality of the electron beam based system (e.g., in addition to other functionality of the system). Alternatively, the electron beam based subsystem described herein may be designed "from scratch" to provide a completely new electron beam based system.

Although the imaging subsystem is described above as being configured as an optical based or electron beam based imaging subsystem, the imaging subsystem may be configured as an ion beam based imaging subsystem. Such a tool may be configured as shown in FIG. 1a except that the electron beam source may be replaced with any suitable ion beam source known in the art. In addition, the imaging subsystem may be any other suitable ion beam based imaging subsystem such as those included in commercially available focused ion beam (FIB) systems, helium ion microscopy (HIM) systems, and secondary ion mass spectroscopy (SIMS) systems.

As noted above, the imaging subsystem is configured for scanning energy (e.g., light or electrons) over a physical version of the specimen thereby generating actual images for the physical version of the specimen. In this manner, the imaging subsystem may be configured as an "actual" imaging subsystem, rather than a "virtual" imaging subsystem. For example, a storage medium (not shown) and computer subsystem(s) 102 shown in FIG. 1 may be configured as a "virtual" system. In particular, the storage medium and the computer subsystem(s) are not part of optical based imaging subsystem 10 and do not have any capability for handling the physical version of the specimen. In other words, in systems configured as virtual systems, the output of its one or more "detectors" may be output that was previously generated by one or more detectors of an actual tool and that is stored in the virtual system, and during the "scanning," the virtual system may replay the stored output as though the specimen is being scanned. In this manner, scanning the specimen with a virtual system may appear to be the same as though a physical specimen is being scanned with an actual system, while, in reality, the "scanning" involves simply replaying output for the specimen in the same manner as the specimen may be scanned. Systems and methods configured as "virtual" inspection systems are described in commonly assigned U.S. Pat. No. 8,126,255 issued on Feb. 28, 2012 to Bhaskar et al. and U.S. Pat. No. 9,222,895 issued on Dec. 29, 2015 to Duffy et al., both of which are incorporated by reference as if fully set forth herein. The embodiments described herein may be further configured as described in these patents. For example, the one or more computer subsystems described herein may be further configured as described in these patents.

Figure 2:
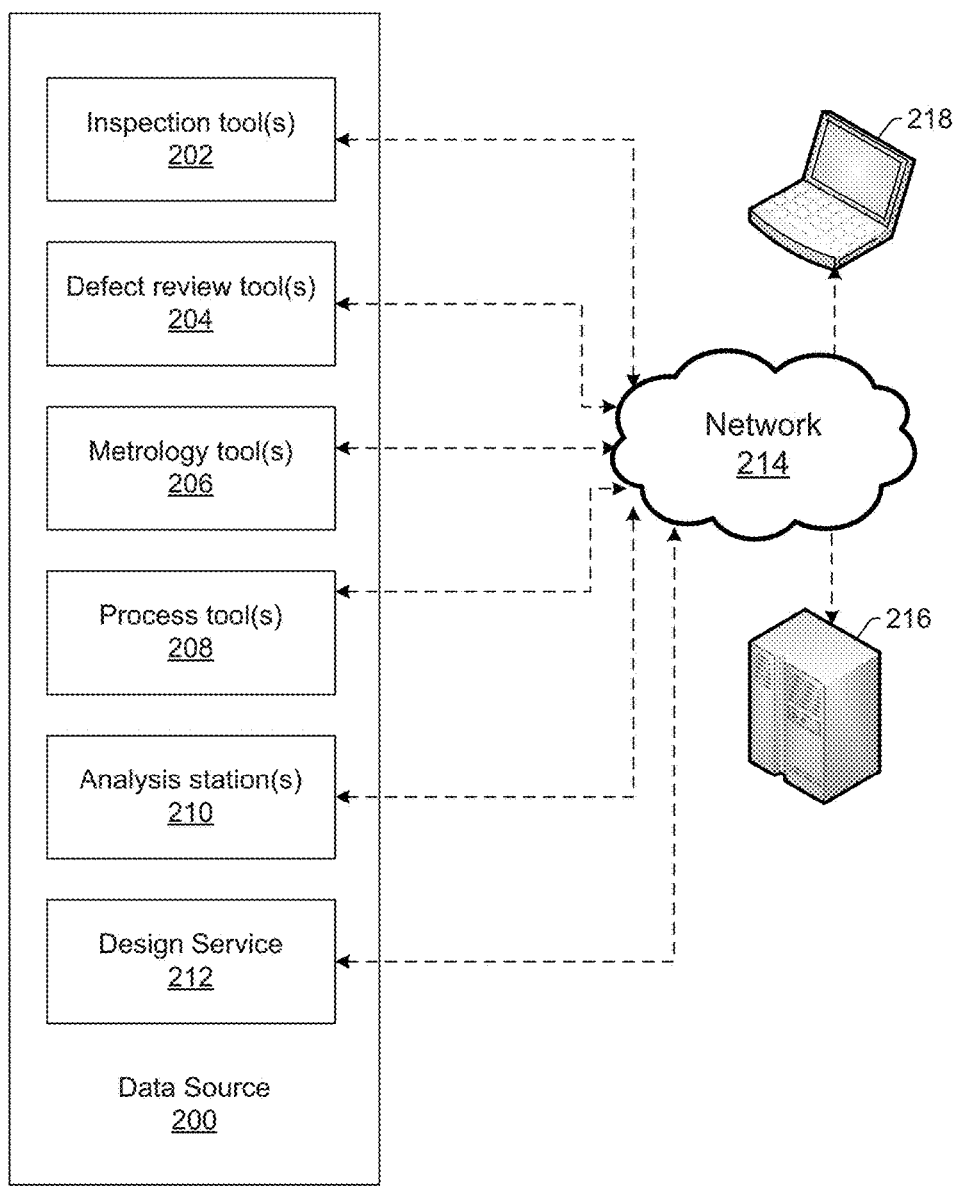
FIG. 2 is a block diagram illustrating another embodiment of a system configured as described herein.

The one or more virtual systems may also be configured as a central compute and storage (CCS) system, which may be configured to perform any of the image analysis and other functions of the computer subsystem(s) described herein. The persistent storage mechanisms described herein can have distributed computing and storage such as the CCS architecture, but the embodiments described herein are not limited to that architecture. One such embodiment is shown in FIG. 2, which illustrates how inspection images optical and scanning electron microscope (SEM) images)) may be used to identify critical issues in semiconductor process and yield improvements as described further herein. In this manner, FIG. 2 shows how inspection and other images can be used in fab data processing. In addition, FIG. 2 shows how inspection and other images can be used in concert with other sources in yield management.

In particular, as shown in FIG. 2, the system may include or be coupled to data source 200, which may include inspection tool(s) 202, defect review tool(s) 204, metrology tool(s) 206, process tool(s) 208, analysis station(s) 210, and design service 212. Each of the elements in data source 200 may be configured to send output generated by the elements to processing unit 216, which may be configured as a CCS, via network 214. User interface 218 such as a laptop computer, personal computer (PC), or other computer systems described herein may also be coupled to each of the elements of data source 200 and/or processing unit 216 via network 214. Processing unit 216 may be configured as one or more of the computer subsystems described herein. Each of the elements of the data source may be configured as described further herein. Network 214 may be further configured as described herein (e.g., as one or more transmission media).

In one such embodiment, inspection tool(s) 202 may include optical based and/or electron beam based inspection tool(s) configured for inspection of specimens such as wafers and/or reticles. The inspection tool(s) may be configured to generate signals, device context, and specimen context. The output produced by the inspection tool(s) may include images, characteristics, features, a noise map, and fault diagnostic control (FDC) or system data from the inspection tool(s) that can be fed into an analysis engine. The areas on the specimens that the inspection tool(s) may be used for generating output include static random access memory (SRAM) and logic areas of the specimens. The layers of the specimens for which the inspection tool(s) may be configured to generate the output include current layers, multiple focal planes, previous layers, and future layers. In addition, the inspection tool(s) may be configured to detect a variety of defect types such as systematic, random, and programmed defects.

Defect review tool(s) 204 may include electron beam or SEM review tool(s) that may be configured to output images and/or measurements of defects detected on a specimen. Metrology tool(s) 206 may include a critical dimension SEM (CDSEM). In addition, the metrology tool(s) may be configured for measuring CD, thickness, refractive index (RI), flatness, resistivity (RS) or sheet resistance, etc. of patterned features or films formed on the specimen. Process tool(s) 208 may be configured to provide a process tool datalog that may include information about one or more processes performed on the specimen such as temperature, flow rate, pressure, illumination, etc. Analysis station(s) 210 may include failure analysis (FA) and/or fab electrical testing tool(s) that may output parametric, functional test values, and the like. Design service 212 may include any suitable source for design data, including any of the design data described herein, such as an electronic design automation (EDA) tool or a computer aided design (CAD) tool, which may include any such suitable commercially available tools known in the art.

Processing unit 216 may have the configuration of a CCS as described above. In addition, processing unit 216 may be configured as a virtual system as described above. Processing unit 216 may be configured to perform one or more functions of the one or more computer subsystems described herein using output generated by one or more of the tools shown in FIG. 2. In addition, the processing unit may be configured to perform one or more additional functions for the specimens using output generated by one or more of the tools shown in FIG. 2. For example, the processing unit may be configured for using output generated by one or more of the tools shown in FIG. 2 for classification of defects detected on the specimens, nuisance filtering of defects detected on the specimens, sampling defects detected on the specimens for defect review and/or providing guidance for defect review of defects detected on the specimens. In addition, the processing unit may be configured for using output generated by one or more of the tools shown in FIG. 2 for optical proximity correction (OPC)/pattern verification and fixing, print checking, recipe set up, real time feedback, process tool monitoring, process monitoring, yield predicting, work in progress (WIP) adjustment, etc.

Processing unit 216 may also be configured for detecting defects and performing other functions described herein using a variety of processing methodologies and output generated by one or more of the tools shown in FIG. 2. For example, the processing unit may be configured for multiple mode inspection (e.g., volumetric and/or multi-focal plane inspection), intra-die inspection, die-to-database inspection, and automatic defect classification (ADC) using output generated by one or more of the tools shown in FIG. 2. The processing unit may also be configured to perform the functions described herein using a variety of algorithm technologies and output generated by one or more of the tools shown in FIG. 2. For example, the processing unit may be configured to perform the one or more functions described herein using output generated by one or more of the tools shown in FIG. 2 and modeling and/or simulation, deep learning (e.g., convolutional neural network (CNN), autoencoder, etc.), correlation, pattern recognition, etc. Processing unit 216 may be further configured as described herein with respect to the one or more computer subsystems.

The processing unit may therefore be configured as a centralized computing storage and analyzer that stores data from various sources. The processing unit may store "big data" and be able to analyze inspection and other images in real time and offline to Characterize images according to usage. In this manner, the processing unit may store post process data and perform post process applications. In addition, the processing unit may be configured for centralized computing that concurrently analyzes data from multiple sources to identify failures, to identify root causes, and to identify corrective actions. The processing unit may also include a combination of hardware and/or software. For example, the processing unit may be configured for centralized computing with a cluster or combination of single and/or multi-core central processing units (CPUs)/graphics processing units (GPUs)/field programmable gate arrays (FPGAs) to achieve the desired computing, especially with a learning based model and/or real time throughput requirements within a fab. As described further above, the processing unit may provide centralized computing with a network to connect with various data sources such as an inspection tool, a process tool, and other processing units that collect data, pre-analyze data, and receive the data as feedback. The processing unit may also be configured for centralized computing with software architecture that enables input data selection for analysis, algorithm selection for analysis, and analysis throughput with selected data and algorithm(s).

The embodiments described herein can be implemented as software features that are either independent of or integrated into actual systems (i.e., systems with specimen handling capability such as inspection systems). As a stand-alone system, the embodiments described herein can also provide data analysis using proprietary inspection image characteristics that can be extracted from inspection images. Such systems can be connected to external data sources or connected to databases such as Klarity systems commercially available from KIA-Tencor that house external data sources.

The CCS may also be created by building hardware infrastructure and software platform(s). For example, networks may be built to connect data sources, which image post process applications may use, such as inspection tools and design data services to a CCS. The CCS hardware infrastructure may provide sufficient storage and computing capacity to enable "big data" analytics including deep learning using the stored images and associated data with extendibility in both computing and storage. The CCS software platform may host multiple image post processing applications simultaneously using distributed "big data" technology in batch and streaming modes invoked from an application program interface (API), interactive user interfaces, and command line interfaces. In addition, the CCS software platform may integrate data sources of inspection, metrology, design, and any other data to the image post process applications within the CCS. The CCS may also be configured to enhance or add data collection capability in all data sources of interest. For example, the CCS may include mechanisms to define selection of data of interest in the data source control software. In addition, the CCS may include mechanisms to collect and output data of interest to the CCS.

In the CCS software architecture, post process applications may include Applications 1, . . . , Application N. The CCS software platform may include proprietary frameworks and open source frameworks (e.g., Hadoop, Spark, Deep learning, etc.). The CCS hardware infrastructure may include CPU, GPU, random access memory (RAM), storage, network, etc.

The data collection method for post processing may be performed using existing software in data sources such as data generation, data acquisition, data selection, and data output. The post processing may also be performed using new software added to data sources including data selection for post process, which may be performed based on data provided by the existing data acquisition software and/or the existing data selection software, and data output for post processing. The post processing may also he performed using the CCS described herein, which may include data ingestion software.

As further noted above, the imaging subsystem may be configured to generate images of the specimen with multiple modes. In general, a "mode" can be defined by the values of parameters of the imaging subsystem used for generating images of a specimen or the output used to generate images of the specimen. Therefore, modes that are different may be different in the values for at least one of the imaging parameters of the imaging subsystem. For example, in one embodiment of an optical based imaging subsystem, at least one of the multiple modes uses at least one wavelength of light for illumination that is different from at least one wavelength of the light for illumination used for at least one other of the multiple modes. The modes may be different in the illumination wavelength as described further herein (e.g., by using different light sources, different spectral filters, etc.) for different modes. In another embodiment, at least one of the multiple modes uses an illumination channel of the imaging subsystem that is different from an illumination channel of the imaging subsystem used for at least one other of the multiple modes. For example, as noted above, the tool may include more than one illumination channel. As such, different illumination channels may be used for different modes.

The optical and electron beam based imaging subsystems described herein may be configured as inspection imaging subsystems. The optical and electron beam based imaging subsystems described herein may also or alternatively be configured as defect review imaging subsystems. The optical and electron beam based imaging subsystems described herein may also or alternatively be configured as metrology imaging subsystems. In particular, the embodiments of the imaging subsystems described herein and shown in FIGS. 1 and 1*a* may be modified in one or more parameters to provide different imaging capability depending on the application for which they will be used. In one such example, the imaging subsystem shown in FIG. 1 may be configured to have a higher resolution if it is to be used for defect review or metrology rather than for inspection. In other words, the embodiments of the imaging subsystems shown in FIGS. 1 and 1*a* describe some general and various configurations for an imaging subsystem that can be tailored in a number of manners that will be obvious to one skilled in the art to produce tools having different imaging capabilities that are more or less suitable for different applications.

In another embodiment, the system may include a semiconductor fabrication tool configured to perform one or more fabrication processes on the specimen. In one such example, as shown in FIG. 1, the system may include semiconductor fabrication tool 106, which may be coupled to computer subsystem(s) 102 and/or any other elements of the system described herein. The semiconductor fabrication tool may include any suitable semiconductor fabrication tool and/or chamber known in the art such as a lithography track, an etch chamber, a chemical mechanical polishing (CMP) tool, a deposition chamber, a stripping or cleaning chamber, and the like. In addition, the semiconductor fabrication tool may include one or more detectors (not shown in FIG. 1) such as those described further herein that are configured to generate output for the specimen. Examples of suitable semiconductor fabrication tools that may be included in the embodiments described herein are described in U.S. Pat. No. 6,891,627 to Levy et al. issued on May 10, 2005, which is incorporated by reference as if fully set forth herein. This patent also describes examples of various detectors that may be included in or coupled to the semiconductor fabrication tool and that can generate output as described further herein. The embodiments described herein may be further configured as described in this patent.

The one or more computer subsystems are configured for acquiring the images generated of the specimen. Acquiring the images may be performed using one of the imaging subsystems described herein (e.g., by directing light or an electron beam to the specimen and detecting light or an electron beam from the specimen). In this manner, acquiring the images may be performed using the physical specimen itself and some sort of imaging hardware (e.g., a wafer inspection and/or defect review tool). In addition, the images may include any of the images described herein (e.g., inspection images, which may be optical or electron beam images, wafer inspection images, reticle inspection images, optical and SEM based defect review images, simulated images, clips from a design layout). However, acquiring the images does not necessarily include imaging the specimen using imaging hardware. For example, another system and/or method may generate the images and may store the generated images in one or more storage media such as a virtual inspection system as described herein or another storage media described herein. Therefore, acquiring the images may include acquiring the images from the storage media in which they have been stored.

The computer subsystem(s) are also configured for determining one or more Characteristics of the acquired images. The characteristic(s) that are determined may include any suitable characteristics of the acquired images such as the images themselves and/or any characteristic(s) (or attribute(s)) that can be derived from the images such as brightness, energy, magnitude, intensity, etc. Such characteristics may be determined in any suitable manner using any suitable algorithm and/or method. While the extraction of inspection and other image characteristics may not necessarily be new, unsupervised generation of characteristics from inspection and other images and identification of anomalies as described further herein is new. Furthermore, the characteristic(s) derived from images to generate defect definitions are new as well.

In one embodiment, the acquired images for which the one or more characteristics are determined are not processed by the one or more computer subsystems prior to the determining step. For example, the embodiments described herein may use non-processed (or parameterized) inspection or other images for device and yield improvement efforts. Inspection or other images may include any of the images described herein such as optical and electron beam based images. Therefore, the output images generated directly from inspection systems (e.g., broadband, laser, and electron beam) and other imaging systems described herein may be fed into an analysis engine for one or more applications. As described further herein, the applications may include correlation of the images or their characteristic(s) to external data such as, but not limited to, electrical test and process tool data, formulating common characteristic(s) among various pattern types independent of image quality, identifying a source mechanism that results in certain characteristics in the images, and predicting device performance or yield relevance.

In this manner, the images for which characteristic(s) are determined may be raw images generated by the detector(s) of an imaging subsystem. However, in some instances, the images for which one or more characteristics are determined may include difference images. The difference images may be generated by subtracting a reference from a test image. The reference and the test image may be two different raw images generated by the imaging subsystem at different locations on the specimen. However, the reference may include any suitable reference known in the art. In the case of optical images, the difference image may be generated from two different optical images generated at different locations on a specimen. In the case of electron beam images, the images may include multiple perspective images, e.g., images acquired from the left, right, top, etc.

The computer subsystem(s) are further configured for identifying anomalies in the images based on the one or more determined characteristics without applying a defect detection algorithm to the images or the one or more characteristics of the images. For example, the computer subsystem(s) may use any or all characteristics of inspection images (such as images, brightness, energy, magnitude, intensity, etc.) to identify anomalies within a die or across a specimen. In this manner, the embodiments described herein may detect anomalies in images generated for a specimen, not necessarily anomalies on a specimen. Any anomalies detected in the images may then be used as described further herein for a variety of applications. Unlike the currently used methods and systems for detecting defects on a specimen, therefore, detecting anomalies in the images does not include applying a defect detection algorithm or threshold(s) to the images or the one or more characteristics of the images. For example, a predetermined defect detection algorithm or threshold(s) is/are not applied to the images or the characteristic(s) to detect the anomalies in the images. In addition, the anomalies detected in the images may or may not correspond to defects on the specimen. Identifying the anomalies in the images may be further performed as described herein.

In contrast to the embodiments described herein, all of the image characteristics may be made available to external processing in raw form so that a user can process and make them available for any defect review or analysis system. However, this approach leaves room for error where complexity of data characteristics such as imaging condition may not be fully known to users. Such an alternate method also limits itself in availability and quality of predefined characteristics.

In one embodiment, the one or more computer subsystems are configured for identifying one or more problems with a device being formed on the specimen based on the identified anomalies. For example, as described further herein, the anomalies detected in the images can be used to identify any problems with a device being formed on the specimen. In this manner, the results produced by the computer subsystems described herein can be used to make device improvements for the device being formed on the specimen (as in an in situ control loop and/or a feedforward control loop) and any other specimens (as in a feedback control loop).

In another embodiment, the one or more computer subsystems are configured for identifying one or more problems with a process performed on the specimen based on the identified anomalies. For example, the computer subsystem(s) may use local image characteristics such as zonal image characteristics to identify potential sources of yield issues that may be related to process, tool, chamber, or process time. Therefore, the embodiments described herein may be capable of detecting issues with a process, process tool, or process time without necessarily detecting defects on the specimen. The zonal image characteristics may be determined in any suitable manner (e.g., based on spatial information associated with the determined characteristic(s)). The process may include any of the processes described herein. In one such example, the zone(s) on a specimen corresponding to abnormal values of characteristic(s) of the images generated for the specimen may be identified. The spatial information for those zone(s) may then be examined to determine if there is a correlation between the zone(s) and the parameters of a process performed on the specimen with a process tool. For example, some process tools may be known to produce particular signatures in characteristics of a specimen when the process tools are functioning correctly versus incorrectly such as film thickness variations in particular areas on a wafer. Therefore, such known specimen characteristic signatures may be compared to image characteristic signatures determined by the computer subsystem(s) described herein. If the spatial characteristics of any of the known specimen characteristic signatures appear to match or substantially match (or otherwise be correlated to) the image characteristic signatures, the performance of the process or process tool may be determined based on the matching known specimen characteristic signature. Identifying the problem(s) with the process may, however, be performed in any suitable manner known in the art.

In a further embodiment, the one or more computer subsystems are configured for altering a process performed on the specimen based on the anomalies to thereby improve yield of the process. For example, information about the anomalies identified in the images generated for the specimen may be used as described further herein to determine problems with the process and/or how the process is performing. That information can then be used to determine how to modify the process if the process appears to not be performing within its predetermined specifications. For example, if there is an abnormality in the image characteristic(s) determined for a specimen, that abnormality may be used to determine how to correct the process to reduce the chances that the abnormality is observed on additional specimens on which the process is performed. Therefore, the process parameter(s) may be altered to improve (i.e., increase) yield of the process.

In some embodiments, the determining is performed in real time while the imaging subsystem is generating the images of the specimen. For example, the computer subsystem(s) described herein may use inspection and other images to extract characteristic(s) in real time both in global and localized behavior within a given inspection or other image, and the characteristic(s) may be further analyzed to identify anomalies in the characteristic(s) that may indicate process or tool problems. In addition, determining the characteristic(s) may include dynamic (in memory or within a learning based model described herein) determination of characteristic(s) from inspection and other images in real time to describe the condition of a given inspection or other image.

In another embodiment, the determining is performed after the imaging subsystem is finished with generating the images of the specimen. For example, the computer subsystem(s) described herein may use inspection and other images to extract characteristic(s) in post processing both in global and localized behavior within a given inspection or other image, and the characteristic(s) may be further analyzed to identify anomalies in the characteristic(s) that may indicate process or tool problems. In this manner, determining the characteristic(s) of the images may include dynamic (in memory or within a learning based model described herein) determination of characteristic(s) from inspection and other images described herein in post processing to describe the condition of a given inspection or other image.

In an additional embodiment, the identifying is performed based on the one or more determined characteristics in combination with one or more parameters of the imaging subsystem used for generating the images. For example, the computer subsystem(s) may be configured for linking image characteristic(s) to inspection or other imaging conditions to further enhance the quality of the image characteristic(s). In addition, the computer subsystem(s) may be configured for using imaging conditions and inspection or other images to identify anomalies among one or more image samples. The one or more parameters of the imaging subsystem may be linked to the image characteristic(s) in any suitable manner.

In one embodiment, the computer subsystem(s) include one or more components executed by the one or more computer subsystems, and the component(s) include a learning based model. For example, as shown in FIG. 1, component(s) 100 executed by the computer subsystem(s), e.g., computer subsystem 36 and/or computer subsystem(s) 102, include learning based model 104. The one or more components may be executed by the computer subsystem(s) in any suitable manner. The learning based model may be further configured as described herein.

In one such embodiment, the model is configured for performing the determining the one or more characteristics of the acquired images and for identifying the one or more characteristics that are determined for the acquired images. For example, the one or more computer subsystems may be configured for algorithm based characteristic extraction from images and/or using a learning based model on specimen images to produce local and/or global characteristic(s) from the images. The characteristic(s) may not be pre-defined, but rather the computer subsystem(s) and/or the learning based model may be configured to determine the one or more characteristics for defect data analysis. Identifying the one or more characteristics that are determined may be performed as described further herein.

In one embodiment, the one or more characteristics of the acquired images include one or more local characteristics of the acquired images. In another embodiment, the one or more characteristics of the acquired images include one or more global characteristics of the acquired images. For example, the computer subsystem(s) may be configured for extracting characteristic(s) based on inspection or other images, or using a learning based model on inspection or other images, to produce local and global characteristics in the inspection or other images. The local characteristics may include zonal image characteristics (e.g., die, wafer, reticle). The local characteristics may be "local" in that they are not determined for an area on the specimen that spans an entirety of the area of the specimen. For example, the local image characteristics may be determined for only a portion of a wafer, only a portion of a die on the wafer, etc. The global characteristics may be "global" in that they may be determined for an entirety of the area of the specimen for which the images were generated.

In some embodiments, the one or more computer subsystems are configured for stacking two or more of the acquired images, detecting defects in the stacked two or more of the acquired images, and determining one or more attributes of the detected defects based on the stacked two or more of the acquired images. For example, the computer subsystem(s) may be configured for stacking images to identify potential defects or to localize defective sites and dynamically generate characteristic(s) of defects. In addition, for a given pattern or defect, multiple images can be stacked to reduce noise and to identify where real failures may be located. Multiple images can be aligned and overlaid using image processing to discern noise from commonality of a given pattern. In one such example, the input to the computer subsystem(s) may include stacked images, e.g., stacked by optics mode, focus, die, pattern, process steps, tools, etc, The computer subsystem(s) may be configured to perform the stacking and analysis in the same neighborhood same optical proximity correction (OPC)). The computer subsystem(s) may be configured for performing such stacking for applications such as defect detection, localizing defects, defect identification independent of die-to-die subtraction, noise reduction, and automatic care area placement for hot spots. Detecting defects in the stacked two or more of the acquired images and determining one or more attributes of the detected defects based on the stacked two or more of the acquired images may be performed in any suitable manner. In other words, the stacked images may be treated as any other images and input to one or more algorithms or methods for detecting defects and determining attributes of the detected defects.

In another embodiment, the one or more characteristics include at least one characteristic of the acquired images linked to parameters of the imaging subsystem used for acquiring the images. For example, the computer subsystem(s) may be configured for linking image characteristic(s) to imaging conditions to further enhance the quality of the image characteristic(s). In one such example, characteristics of images of patterns may vary based on imaging conditions. Therefore, once characteristics of certain patterns are identified, the quality of the image characteristics may be enhanced by controlling imaging conditions. In this manner, the image quality can be improved by controlling image conditions.

In one embodiment in which the computer subsystem(s) include component(s) that include a learning based model, the one or more computer subsystems are configured for training the learning based model with the acquired images and one or more additional types of information for the specimen, and the learning based model is configured for predicting information for defects on the specimen based on the acquired images and the one or more additional types of the information. In this manner, defect definition is no longer based on a characteristic or a set of characteristics exceeding certain values just among inspection parameters. A defect can be identified as having conditions where a characteristic or set of characteristics exhibit non-typical signature when individual values or index are deviating from expected behavior or the output from the learning based model is beyond the "normal baseline" and therefore abnormal. For instance, higher sigma in magnitude within a die may be considered an anomaly and therefore would be further processed with other constituents such as that described further herein to identify failure mode.

In addition, the computer subsystem(s) may be configured for characteristic based thresholding. For example, a defect may no longer be an open or a short but a marginal pattern and characteristic(s) with certain threshold can be used for disposition. Such defect detection may be performed for applications such as process monitoring and inline yield prediction.

The learning based model may also be configured for defect location, comparing identical patterns, and common modes of failure or variation. For example, defects can be classified based on physical appearance, elemental composition, design, etc. The term "common modes" here refers to common failure mechanisms such as process conditions or OPC treatment. Multiple patterns may fail where the cause of failures may be the same but classified differently. For instance, often several image types may fail, but they may all be related to the way sub-resolution assist features (SRAFs) were applied to a design. Another common mode may be a case where different failures are attributed to similar proximity of neighboring polygons or that one or more inspection attributes are similar among different pattern types.

The learning based model may also be configured as a relational database. The learning based model may further be configured for correlation, characteristics extraction, pattern analysis, etc. For example, the learning based model may be configured as a statistical data analysis engine or machine learning system. The learning based model may be configured for data mining or knowledge discovery in databases (KDD) using a variety of sources such as statistics, pattern recognition, neuro-computing, machine learning, artificial intelligence (AI), and any other databases available to the learning based model. KDD refers to the broad process of finding knowledge in data. In this manner, a learning based model may be used in conjunction with specimen images to identify defects or anomalies in processing. In addition, the embodiments described herein may be configured for a combination of image based analysis, data mining, and deep learning techniques performed using inspection and other images and extraction of characteristic(s) from the images. The learning based model may also be configured to perform yield impact analysis, source isolation, prediction, and classification, each of which may be performed as described further herein.

In one such embodiment, the one or more additional types of information for the specimen include design data for the specimen. For example, the learning based model may be configured for identifying defects based on an external response variable such as design. In one such example, the learning based model may be configured to use specimen images in conjunction with external response variables such as design to build a learning based model for correlation and predictions both in supervised and unsupervised approaches. The learning based model can be built based on, but not limited to, deep learning techniques such as CNN, autoencoder, or any deep learning architecture applicable to the applications described herein.

In another such embodiment, the one or more additional types of information for the specimen include electrical test and measurement data for the specimen. The electrical test and measurement data may include any suitable electrical data such as electrical test data produced by any suitable electrical testing of the specimen. For example, the learning based model may be configured for identifying defects based on an external response variable such as electrical test data. In one such example, the learning based model may be configured to use specimen images in conjunction with external response variables such as electrical data to build a learning based model for correlation and predictions both in supervised and unsupervised approaches. In this manner, the embodiments described herein may be configured as a functional engine that utilizes the images and external data sources for storage and data processing. In addition, the embodiments described herein may be configured as a functional engine that enables both supervised and unsupervised approaches that enable identification of critical issues in process and in predicting the impact to device performance and yield. The learning based model can be built based on, but not limited to, deep learning techniques such as CNN, autoencoder, or any deep learning architecture applicable to the applications described herein.

In a further such embodiment, the one or more additional types of information for the specimen include process tool data for the specimen. For example, the learning based model may be configured for identifying defects based on an external response variable such as process tool data. In one such example, the learning based model may be configured to use specimen images in conjunction with external response variables such as process tool data to build a learning based model for correlation and predictions both in supervised and unsupervised approaches. The learning based model can be built based on, but not limited to, deep learning techniques such as CNN, autoencoder, or any deep learning architecture applicable to the applications described herein.

The computer subsystem(s) and/or the learning based model may also be configured to perform one or more additional functions using the external response variables. For example, the computer subsystem(s) and/or the learning based model may be configured for using one or more of the image characteristic(s) or the images themselves in combination with other response variables (e.g., electrical test or tool data) to define defect or criticality to yield and device performance. Defining defects or criticality to yield and device performance may be otherwise performed as described further herein.

In one such example, the input to the computer subsystem(s) may include images plus characteristic(s) for one or more layers and/or one or more devices, The computer subsystem(s) may be configured for grouping and/or threshold setting using such input. Grouping and/or threshold setting may be performed for applications such as binning and/or grading, defect definition, determining severity of failure.

In another such example, the input to the computer subsystem(s) may include images (optical and electron beam images), characteristic(s), and electrical and functional test data for one or more layers and/or one or more devices. The computer subsystem(s) may be configured for advanced correlation modeling such as data mining or neural network (NN) using the input. In addition, or alternatively, the computer subsystem(s) may be configured for determining defects not solely by the inspection data using such inputs. The computer subsystem(s) may perform such functions for defect definition, sampling for review and metrology, inspection optimization, and yield prediction.

In an additional such example, the input to the computer subsystem(s) may include images (e.g., optical and electron beam images), characteristic(s), and process tool datalog(s) for one or more layers and/or one or more devices. The computer subsystem(s) may be configured to use such input for generating a model to define the impact of processing conditions to changes in inspection image characteristics. The computer subsystem(s) may generate such a model for applications including in situ monitoring and in situ process optimization.

In another example, the input to the computer subsystem(s) may include common characteristics from multiple images. The computer subsystem(s)) may be configured to use one or a set of characteristics with similar behavior to group devices. Such functions may be performed tor applications such as inspection and/or metrology set up, in situ process adjustments, and yield correlation.

The embodiments described herein may or may not be configured for training the learning based model(s) described herein. For example, another method and/or system may be configured to generate a trained learning based model, which can then be accessed and used by the embodiments described herein.

In some such embodiments, the training includes supervised training. For example, in the case of a CNN, during the training phase, training data (e.g., test, reference, design, etc.) may be input to defect detection and/or classification and manual defect review. The defect detection may be performed using any suitable defect detection algorithms such as MDAT, which is used by some inspection tools that are commercially available from KLA-Tencor. Defect classification may be performed using any suitable classification method such as aligning the defect images to design and classifying the defects based on the design data corresponding to the defect location. Manual defect review may be performed by a user in any suitable manner known in the art. The CNN may then be trained based on the results of the defect detection and/or classification and manual review. In particular, the failure modes can be defined by inputting sampled failed images and allowing the system to identify failure modes, which may be used in classifying other patterns or defects. The results of the training may be a trained CNN. During runtime then, a test image may be input to the trained CNN and the output of the trained CNN may include a defect prediction, a defect classification, etc.

In one such embodiment, the input may include images (inspection and other images) from one or more devices and/or one or more layers on a specimen. The one or more components may include a CNN, a deep learning model configured for image analysis and/or characteristic extraction, and/or self-organizing maps. The one or more components and/or the one or more computer subsystems may be configured for supervised learning and use, excursion detection, common failure mode identification, static and adaptive sampling for defect review and metrology, failure mode and source identification, tool and yield monitoring, and model and rule generation. For example, in a supervised approach, the image(s) may be compared to information in a database (which may include multiple data sources). Results of the comparison may be used for failure mode identification.

In another example of supervised detection and classification, user labeled reference and test images may be input to a CNN. The user may label the defects by looking at review tool images. The CNN may be configured as described herein. In the supervised detection and classification approach, the $i^{th}$ output neuron of the CNN may have high activation for defect class i. In such an approach, the design image at a defect location may optionally be input to the CNN. The design image at the defect location may also be optionally input to a geometry extractor. The geometry extractor may produce a geometry encoded image that may also be optionally input to the CNN for the supervised detection and classification.

Applications of supervised classification include review sampling, recipe optimization (e.g., threshold optimization, micro care area generation for design data, etc.), tool monitoring (e.g., critical location property wafer level map, critical location attribute derived from inspection images), metrology (e.g., analysis of stacked die attributes derived from inspection images), yield monitoring (e.g., correlation of inspection image characteristics to yield), and criticality rule finding (e.g., correlation of design attributes to inspection image characteristics).

In additional such embodiments, the training includes unsupervised training. For example, the input to the learning based model may include unlabeled inputs (in that the inputs are not labeled as defects or not defects). With a mixture of defective and non-defective sites, a learning based model such as an autoencoder can self-organize data based on their characteristic(s) and classify defects without supervision. Once the data can be classified according to self-organizing characteristic(s), then the data can be grouped or separated automatically.

In one such embodiment, the input may include images (e.g., inspection and other images) from one or more devices and/or one or more layers on a specimen. The one or more components may include a CNN, a deep learning model configured for image analysis and/or characteristic extraction, and/or self-organizing maps. The one or more components and/or the one or more computer subsystems may be configured for unsupervised learning and usage, adaptive learning, intra-die inspection, die, reticle, and wafer level signature identification, and identification of abnormal pattern (signature) to identify unknown excursions. For example, in an unsupervised approach, the image(s) may be used to generate one or more self-organized maps. The self-organized maps may be used to identify common failure modes and/or excursions. The identified common failure modes and/or excursions can be used for device improvement.

In one such example of unsupervised classification, the input to an autoencoder may include an unlabeled inspection lot, which may include inspection reference images and inspection defect images. In the unsupervised classification approach, the autoencoder may have a set of output neurons. In this manner, an autoencoder can be used as a deep unsupervised learning NN. In such an approach, the design image at a defect location may optionally be input to the autoencoder. The design image at the defect location may also be optionally input to a geometry extractor. The geometry extractor may produce a geometry encoded image that may also be optionally input to the autoencoder for the unsupervised detection and classification.

Applications of unsupervised classification include user-guided adaptive review sampling (e.g., output of neurons corresponding to fuzzy clusters of input images, review images corresponding to the maximum activation of each output neuron that is presented to the user, who may dynamically adjust what he/she wants to sample, etc.), intra-die inspection with inspection images of the same pattern of interest (POI) (e.g., outlier detection using output neuron activation values), wafer signature identification (e.g., outlier detection with POI inspection images across a wafer), and power assisted defect sampling and labeling for supervised classification. Outlier detection using output neuron activation values may be performed when analyzing a pattern or a defect using an image of the same pattern. For example, there may be certain expected characteristics for a given pattern. When a pattern is normal, it should exhibit similar properties that are expected for the given pattern. Once a pattern deviates from the expected properties, the sample would be considered an outlier based on the neuron activation values (e.g., characteristic(s) or property/properties of a given pattern).

The learning based model may include a machine learning model. Machine learning can be generally defined as a type of artificial intelligence (AI) that provides computers with the ability to learn without being explicitly programmed. Machine learning focuses on the development of computer programs that can teach themselves to grow and change when exposed to new data. In other words, machine learning can be defined as the subfield of computer science that "gives computers the ability to learn without being explicitly programmed." Machine learning explores the study and construction of algorithms that can learn from and make predictions on data—such algorithms overcome following strictly static program instructions by making data driven predictions or decisions, through building a model from sample inputs.

The machine learning described herein may be further performed as described in "Introduction to Statistical Machine Learning," by Sugiyama, Morgan Kaufmann, 2016, 534 pages; "Discriminative, Generative, and Imitative Learning," Jebara, MIT Thesis, 2002, 212 pages; and "Principles of Data Mining (Adaptive Computation and Machine Learning)," Hand et al., MIT Press, 2001, 578 pages; which are incorporated by reference as if fully set forth herein. The embodiments described herein may be further configured as described in these references.

In another such embodiment, the learning based model includes a deep learning based model, Generally speaking, "deep learning" (also known as deep structured learning, hierarchical learning or deep machine learning) is a branch of machine learning based on a set of algorithms that attempt to model high level abstractions in data. In a simple case, there may be two sets of neurons: ones that receive an input signal and ones that send an output signal. When the input layer receives an input, it passes on a modified version of the input to the next layer. In a deep network, there are many layers between the input and output (and the layers are not made of neurons but it can help to think of it that way), allowing the algorithm to use multiple processing layers, composed of multiple linear and non-linear transformations.

Deep learning is part of a broader family of machine learning methods based on learning representations of data. An observation (e.g., an image) can be represented in many ways such as a vector of intensity values per pixel, or in a more abstract way as a set of edges, regions of particular shape, etc. Some representations are better than others at simplifying the learning task (e.g., face recognition or facial expression recognition). One of the promises of deep learning is replacing handcrafted features with efficient algorithms for unsupervised or semi-supervised feature learning and hierarchical feature extraction.

Research in this area attempts to make better representations and create models to learn these representations from large-scale unlabeled data. Some of the representations are inspired by advances in neuroscience and are loosely based on interpretation of information processing and communication patterns in a nervous system, such as neural coding which attempts to define a relationship between various stimuli and associated neuronal responses in the brain.

Various deep learning architectures such as deep neural networks, convolutional deep neural networks, deep belief networks and recurrent neural networks have been applied to fields like computer vision, automatic speech recognition, natural language processing, audio recognition and bioinformatics where they have been shown to produce state-of-the-art results on various tasks.

In a further embodiment, the learning based model includes a neural network. For example, the model may be a deep neural network with a set of weights that model the world according to the data that it has been fed to train it. Neural networks can be generally defined as a computational approach which is based on a relatively large collection of neural units loosely modeling the way a biological brain solves problems with relatively large clusters of biological neurons connected by axons. Each neural unit is connected with many others, and links can be enforcing or inhibitory in their effect on the activation state of connected neural units. These systems are self-learning and trained rather than explicitly programmed and excel in areas where the solution or feature detection is difficult to express in a traditional computer program.

Neural networks typically consist of multiple layers, and the signal path traverses from front to back. The goal of the neural network is to solve problems in the same way that the human brain would, although several neural networks are much more abstract. Modern neural network projects typically work with a few thousand to a few million neural units and millions of connections. The neural network may have any suitable architecture and/or configuration known in the art.

In another embodiment, the learning based model includes a CNN. For example, the embodiments described herein can take advantage of deep learning concepts such as a CNN to solve the normally intractable representation conversion problem (e.g., rendering). The model may have any CNN configuration or architecture known in the art.

In a further embodiment, the learning based model includes a deep neural network. For example, the model may be configured to have a deep learning architecture in that the model may include multiple layers, which perform a number of algorithms or transformations. In general, the number of layers in the model is not significant and is use case dependent. For practical purposes, a suitable range of layers included in the model is from 2 layers to a few tens of layers. The deep neural network may be otherwise configured as described herein. In one such embodiment, the learning based model may be configured as a deep CNN (DCNN) as described in "ImageNet Classification with Deep Convolutional Neural Networks," by Krizhevsky et al., NIPS, 2012, 9 pages, which is incorporated by reference as if fully set forth herein. The embodiments described herein may be further configured as described in this reference.

In an additional embodiment, the learning based model includes a discriminative model. Discriminative models, also called conditional models, are a class of models used in machine learning for modeling the dependence of an unobserved variable y on an observed variable x. Within a probabilistic framework, this is done by modeling the conditional probability distribution $P(y|x)$, which can be used for predicting y from x. Discriminative models, as opposed to generative models, do not allow one to generate samples from the joint distribution of x and y. However, for tasks such as classification and regression that do not require the joint distribution, discriminative models can yield superior performance. On the other hand, generative models are typically more flexible than discriminative models in expressing dependencies in complex learning tasks. In addition, most discriminative models are inherently supervised and cannot easily be extended to unsupervised learning. Application specific details ultimately dictate the suitability of selecting a discriminative versus generative model. The discriminative model may be further configured as described in the reference incorporated above by Krizhevsky. In this manner, the embodiments described herein may use a deep learning network of a discriminative type for the applications described herein (classification or regression purposes).

In some embodiments, the learning based model includes a generative model. A "generative" model can be generally defined as a model that is probabilistic in nature. In other words, a "generative" model is not one that performs forward simulation or rule-based approaches and, as such, a model of the physics of the processes involved in generating an actual image (for which a simulated image is being generated) is not necessary. Instead, as described further herein, the generative model can be learned (in that its parameters can be learned) based on a suitable training set of data. The generative model may be further configured as described in U.S. patent application Ser. No. 15/176,139 by Zhang et al. filed Jun. 7, 2016, which is incorporated as if fully set forth herein. The embodiments described herein may be further configured as described in this patent application. In this manner, the embodiments described herein may use a deep learning network such as a deep generative network for the applications described herein (classification or regression purposes).

In one embodiment, the learning based model includes a deep generative model. For example, the model may be configured to have a deep learning architecture in that the model may include multiple layers, which perform a number of algorithms or transformations. In general, the number of layers on one or both sides of the generative model is not significant and is use case dependent. For practical purposes, a suitable range of layers on both sides is from 2 layers to a few tens of layers.

In another such embodiment, the learning based model includes an autoencoder. An autoencoder, autoassociator or Diabolo network is an artificial neural network used for unsupervised learning of efficient codings. The aim of an autoencoder is to learn a representation (encoding) for a set of data, typically for the purpose of dimensionality reduction. Recently, the autoencoder concept has become more widely used for learning generative models of data. Architecturally, the simplest form of an autoencoder is a feedforward, non-recurrent neural network very similar to the multilayer perceptron (MLP)—having an input layer, an output layer and one or more hidden layers connecting them—, but with the output layer having the same number of nodes as the input layer, and with the purpose of reconstructing its own inputs (instead of predicting the target value given inputs). Therefore, autoencoders are unsupervised learning models. An autoencoder always consists of two parts, the encoder and the decoder. Various techniques exist to prevent autoencoders from learning the identity function and to improve their ability to capture important information and learn richer representations. The autoencoder may include any suitable type of autoencoder such as a Denoising autoencoder, sparse autoencoder, variational autoencoder, and contractive autoencoder.

In one embodiment, the computer subsystem(s) are configured for predicting defect information for the specimen based on the one or more determined characteristics and one or more additional types of information for the specimen. For example, the one or more computer subsystems may be configured to use one or more image characteristics or the images themselves combined with other response variables (e.g., electrical test or tool data) to define defects on the specimen. In particular, correlations between the external response variables and the image characteristic(s) can be determined. The image characteristic(s) and the correlations can then be used to predict defects on the specimen without the external response variables and/or without applying a defect detection algorithm to the images generated for the specimen. In addition, as described further herein, once anomalies in the image characteristic(s) have been identified by the computer subsystem(s) as described further herein, the external response variables may be used to identify the anomalies in the image characteristic(s) that correspond to defects and the anomalies in the image characteristic(s) that do not correspond to defects on the specimen.

In another embodiment, the computer subsystem(s) are configured for predicting yield criticality of defects on the specimen based on the one or more determined characteristics and one or more additional types of information for the specimen. For example, the one or more computer subsystems may be configured to use one or more image characteristics or the images themselves combined with other response variables (e.g., electrical test or tool data) to define defect criticality to yield. In one such example, the image characteristic(s) and the other response variables can be used to determine the effect that the defects will have on the device being formed on the specimen and therefore on the yield of the process being performed to fabricate the device on the specimen.

In an additional embodiment, the computer subsystem(s) are configured for predicting performance of devices being formed on the specimen based on the one or more determined characteristics and one or more additional types of information for the specimen. For example, the one or more computer subsystems may be configured to use one or more image characteristics or the images themselves combined with other response variables (e.g., electrical test or tool data) to predict device performance. In one such example, the image characteristic(s) and the other response variables can be used to determine the effect that the defects will have on the device being formed on the specimen and therefore on the performance of the devices being formed on the specimen.

In some embodiments, the computer subsystem(s) are configured for creating the one or more characteristics in real time based on one or more additional types of information. For example, the computer subsystem(s) may be configured for real time creation of relevant characteristic(s) based on response variables (e.g., defect type such as open or bridge, nuisance, etc.). In this manner, the computer subsystem(s) may not be configured to generate a predetermined characteristic or predetermined set of characteristics. Instead, the embodiments described herein can be configured to analyze any and all of the image characteristics that can be determined from the specimen images and can be configured to select one or more of the characteristics for anomaly identification and/or other steps described herein based on the response variables.

In one embodiment, the computer subsystem(s) are configured for performing the acquiring, determining, and identifying steps for multiple specimens, monitoring the one or more characteristics of the anomalies for changes, and altering a parameter of a process tool in response to the changes detected by the monitoring. For example, the computer subsystem(s) may be configured to use a change in pattern (behavior) of image characteristic(s) to detect problems and apply subsequent changes to processing tools. In other words, when the image characteristic(s) of specimens appear to drift over time (or exhibit a dramatic change from one specimen to another), the change in the image characteristic(s) may be identified as corresponding to a potential problem in the process performed on the specimen. The change in the image characteristic(s) can then be used to determine how to change the process to return the image characteristic(s) to their original values.

In another embodiment, the one or more computer subsystems are configured for determining one or more spatial characteristics of the anomalies and identifying a potential source of the anomalies based on the determined one or more spatial characteristics. For example, the computer subsystem(s) may use local image characteristics such as zonal image characteristics to identify potential sources of yield issues that may be related to process, tool, chamber, or process time. In this manner, the input to the steps performed by the computer subsystem(s) may include spatial and time distribution of inspection images across a wafer/reticle/die, etc. The spatial patterns may represent different potential failure modes due to process/tool variations. The spatial patterns can then be used for process monitoring, tool monitoring, and process improvement based on a correlation between the spatial patterns and the process parameters, the tool parameters, and the process. The correlation may be determined in any suitable manner (e.g., experimentally or theoretically).

In an additional embodiment, the computer subsystem(s) are configured for stacking two or more of the acquired images and identifying one or more weak points in a design for the specimen based on the stacked two or more of the acquired images. For example, the computer subsystem(s) may be configured for using stacked images to identify weak points in a design. In particular, when more than one specimen image are overlaid with each other (i.e., stacked), any anomalies or defects that appear repeatedly at more than one instance of the same within design location or at more than one instance of the same patterned feature in the design indicate that that within design location or patterned feature is a weak point in the design (i.e., that location or patterned feature appears to be more susceptible to defects than other locations or patterned features in the design).

In a further embodiment, the computer subsystem(s) are configured for creating an index based on the one or more characteristics of the acquired images representing potential impact of one or more attributes of the specimen, corresponding to the one or more characteristics of the images, on performance of devices being formed on the specimen. For example, the computer subsystem(s) may be configured for using one or more of the image characteristics to formulate an index for potential impact to device performance. In one such example, an abnormality index may be determined based on one or more characteristics from the images. When normalized, the potential risk of each device may be predicted using the characteristic(s) determined from the images. In this manner, the index may be used for device evaluation and/or ranking based on severity of abnormality.

The embodiments described herein have a number of advantages over currently used methods and systems. For example, using inspection and other images described herein and their characteristics as described herein provides additional sensitivity to manufacturing issues. Using images and their characteristics as described herein can reduce false positives (irrelevant events) and missed real problems (yield relevant issues) by maximizing the information available in the images. Rather than relying on reported defects or a set of predefined characteristics, use of the images allows discovery of hidden problems by using advanced correlation engines of unsupervised data mining such as neural networks and deep learning. Furthermore, by using images, a user can take advantage of advancement in data processing or correlation engines where new characteristics can be dynamically extracted for improved modeling and applications.

Each of the embodiments of each of the systems described above may be combined together into one single embodiment.

Another embodiment relates to a computer-implemented method for detecting anomalies in images of a specimen. The method includes generating images of a specimen by directing energy to and detecting energy from the specimen with an imaging subsystem. The imaging subsystem includes at least one energy source configured for generating the energy directed to the specimen and at least one detector configured for detecting the energy from the specimen. The method also includes acquiring the images generated of the specimen and determining one or more characteristics of the acquired images. In addition, the method includes identifying anomalies in the images based on the one or more determined characteristics without applying a defect detection algorithm to the images or the one or more characteristics of the images. The acquiring, determining, and identifying steps are performed by one or more computer subsystems coupled to the imaging subsystem.

Each of the steps of the method may be performed as described further herein. The method may also include any other step(s) that can be performed by the system, imaging subsystem, computer subsystem(s), component(s), and/or model(s) described. herein. The imaging subsystem, one or more computer systems, one or more components, and model may be configured according to any of the embodiments described herein, e.g., imaging subsystem 10, computer subsystem(s) 102, component(s) 100, and model 104, respectively. In addition, the method described above may be performed by any of the system embodiments described herein.

Figure 3:
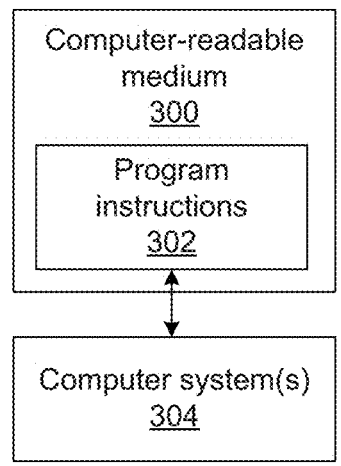
FIG. 3 is a block diagram illustrating one embodiment of a non-transitory computer-readable medium storing program instructions for causing one or more computer systems to perform a computer-implemented method described herein.

An additional embodiment relates to a non-transitory computer-readable medium storing program instructions executable on one or more computer systems for performing a computer-implemented method for detecting anomalies in images of a specimen. One such embodiment is shown in FIG. 3. In particular, as shown in FIG. 3, non-transitory computer-readable medium 300 includes program instructions 302 executable on computer system(s) 304. The computer-implemented method may include any step(s) of any method(s) described herein.

Program instructions 302 implementing methods such as those described herein may be stored on computer-readable medium 300. The computer-readable medium may be a storage medium such as a. magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes is ("MFC"), SSE (Streaming SIMD Extension) or other technologies or methodologies, as desired.

Computer system(s) 304 may be configured according to any of the embodiments described herein.

Further modifications and alternative embodiments of various aspects of the invention will be apparent to those skilled in the art in view of this description. For example, methods and systems for detecting anomalies in images of a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect anomalies in images of a specimen, comprising:
    an imaging subsystem configured for generating images of a specimen by directing energy to and detecting energy from the specimen, wherein the imaging subsystem comprises at least one energy source configured for generating the energy directed to the specimen and at least one detector configured for detecting the energy from the specimen; and
    one or more computer subsystems coupled to the imaging subsystem, wherein the one or more computer subsystems are configured for:
        acquiring the images generated of the specimen, wherein the acquired images comprise optical images or electron beam images;
        determining one or more characteristics of the acquired images; and identifying anomalies in the optical images or the electron beam images based on the one or more determined characteristics without applying a predetermined defect detection algorithm to the images or the one or more characteristics of the images, and wherein the one or more computer subsystems comprise one or more components executed by the one or more computer subsystems, and wherein the one or more components comprise a learning based model configured for performing said determining the one or more characteristics of the acquired images and for identifying the one or more characteristics that are determined for the acquired images.

2. The system of claim 1, wherein the acquired images for which the one or more characteristics are determined are not processed by the one or more computer subsystems prior to said determining.

3. The system of claim 1, wherein the one or more computer subsystems are further configured for identifying one or more problems with a device being formed on the specimen based on the identified anomalies.

4. The system of claim 1, wherein the one or more computer subsystems are further configured for identifying one or more problems with a process performed on the specimen based on the identified anomalies.

5. The system of claim 1, wherein the one or more computer subsystems are further configured for altering a process performed on the specimen based on the anomalies to thereby improve yield of the process.

6. The system of claim 1, wherein said determining is performed in real time while the imaging subsystem is generating the images of the specimen.

7. The system of claim 1, wherein said determining is performed after the imaging subsystem is finished generating the images of the specimen.

8. The system of claim 1, wherein said identifying is performed based on the one or more determined characteristics in combination with one or more parameters of the imaging subsystem used for generating the images.

9. The system of claim 1, wherein the one or more characteristics of the acquired images comprise one or more local characteristics of the acquired images.

10. The system of claim 1, wherein the one or more characteristics of the acquired images comprise one or more global characteristics of the acquired images.

11. The system of claim 1, wherein the one or more computer subsystems are further configured for stacking two or more of the acquired images, detecting defects in the stacked two or more of the acquired images, and determining one or more attributes of the detected defects based on the stacked two or more of the acquired images.

12. The system of claim 1, wherein the one or more characteristics comprise at least one characteristic of the acquired images linked to parameters of the imaging subsystem used for acquiring the images.

13. The system of claim 1, wherein the one or more computer subsystems are further configured for training the learning based model with the acquired images and one or more additional types of information for the specimen, and wherein the learning based model is further configured for predicting information for defects on the specimen based on the acquired images and the one or more additional types of the information.

14. The system of claim 13, wherein the one or more additional types of information for the specimen comprise design data for the specimen.

15. The system of claim 13, wherein the one or more additional types of information for the specimen comprise electrical test and measurement, data for the specimen.

16. The system of claim 13, wherein the one or more additional types of information for the specimen comprise process tool data for the specimen.

17. The system of claim 13, wherein the training comprises supervised training.

18. The system of claim 13, wherein the training comprises unsupervised training.

19. The system of claim 13, wherein the learning based model comprises a deep learning based model.

20. The system of claim 13, wherein the learning based model comprises a convolutional neural network.

21. The system of claim 13, wherein the learning based model comprises an autoencoder.

22. The system of claim 1, wherein the one or more computer subsystems are further configured for predicting defect information for the specimen based on the one or more determined characteristics and one or more additional types of information for the specimen.

23. The system of claim 1, wherein the one or more computer subsystems are further configured for predicting yield criticality of defects on the specimen based on the one or more determined characteristics and one or more additional types of information for the specimen.

24. The system of claim 1, wherein the one or more computer subsystems are further configured for predicting performance of devices being formed on the specimen based on the one or more determined characteristics and one or more additional types of information for the specimen.

25. The system of claim 1, wherein the one or more computer subsystems are further configured for creating the one or more characteristics in real time based on one or more additional types of information.

26. The system of claim 1, wherein the one or more computer subsystems are further configured for performing said acquiring, determining, and identifying for multiple specimens, monitoring the one or more characteristics or the anomalies for changes, and altering a parameter of a process tool in response to the changes detected by the monitoring.

27. The system of claim 1, wherein the one or more computer subsystems are further configured for determining one or more spatial characteristics of the anomalies and identifying a potential source of the anomalies based on the determined one or more spatial characteristics.

28. The system of claim 1, wherein the one or more computer subsystems are further configured for stacking two or more of the acquired images and identifying one or more weak points in a design for the specimen based on the stacked two or more of the acquired images.

29. The system of claim 1, wherein the one or more computer subsystems are further configured for creating an index based on the one or more characteristics of the acquired images representing potential impact of one or more attributes of the specimen, corresponding to the one or more characteristics of the images, on performance of devices being formed on the specimen.

30. The system of claim 1, wherein the imaging subsystem is further configured as an optical based imaging subsystem.

31. The system of claim 1, wherein the imaging subsystem is further configured as an electron beam based imaging subsystem.

32. The system of claim 1, wherein the specimen is a wafer.

33. The system of claim 1, wherein the specimen is a reticle.

34. A non-transitory computer-readable medium, storing program instructions executable on one or more computer systems for performing a computer-implemented method for detecting anomalies in images of a specimen, wherein the computer-implemented method comprises:

generating images of a specimen by directing energy to and detecting energy from the specimen with an imaging subsystem, wherein the imaging subsystem comprises at least one energy source configured for generating the energy directed to the specimen and at least one detector configured for detecting the energy from the specimen;

acquiring the images generated of the specimen, wherein the acquired images comprise optical images or electron beam images;

determining one or more characteristics of the acquired images; and identifying anomalies in the optical images or the electron beam images based on the one or more determined characteristics without applying a predetermined defect detection algorithm to the images or the one or more characteristics of the images, wherein said acquiring, said determining, and said identifying are performed by one or more computer subsystems coupled to the imaging subsystem, wherein the one or more computer subsystems comprise one or more components executed by the one or more computer subsystems, and wherein the one or more components comprise a learning based model configured for performing said determining the one or more characteristics of the acquired images and for identifying the one or more characteristics that are determined for the acquired images.

35. A computer-implemented method for detecting anomalies in images of a specimen, comprising generating images of a specimen by directing energy to and detecting energy from the specimen with an imaging subsystem, wherein the imaging subsystem comprises at least one energy source configured for generating the energy directed to the specimen and at least one detector configured for detecting the energy from the specimen;

acquiring the images generated of the specimen, wherein the acquired images comprise optical images or electron beam images;

determining one or more characteristics of the acquired images; and identifying anomalies in the optical images or the electron beam images based on the one or more determined characteristics without applying a predetermined defect detection algorithm to the images or the one or more characteristics of the images, wherein said acquiring, said determining, and said identifying are performed by one or more computer subsystems coupled to the imaging subsystem, wherein the one or more computer subsystems comprise one or more components executed by the one or more computer subsystems, and wherein the one or more components comprise a learning based model configured for performing said determining the one or more characteristics of the acquired images and for identifying the one or more characteristics that are determined for the acquired images.

* * * * *